(12) United States Patent
Pelc

(10) Patent No.: US 9,488,739 B2
(45) Date of Patent: Nov. 8, 2016

(54) SPECTRAL IMAGING SYSTEM AND METHOD

(71) Applicant: The Board of Trustees of the Leland Stanford Junior University, Palo Alto, CA (US)

(72) Inventor: Norbert J. Pelc, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 216 days.

(21) Appl. No.: 14/574,103

(22) Filed: Dec. 17, 2014

(65) Prior Publication Data

US 2015/0168570 A1 Jun. 18, 2015

Related U.S. Application Data

(60) Provisional application No. 61/917,929, filed on Dec. 18, 2013.

(51) Int. Cl.
| | |
|---|---|
| *G01N 23/00* | (2006.01) |
| *G01T 1/24* | (2006.01) |
| *G01N 23/04* | (2006.01) |
| *A61B 6/00* | (2006.01) |
| *A61B 6/03* | (2006.01) |

(52) U.S. Cl.
CPC .............. *G01T 1/247* (2013.01); *A61B 6/4241* (2013.01); *G01N 23/046* (2013.01); *A61B 6/032* (2013.01); *A61B 6/482* (2013.01); *A61B 6/483* (2013.01); *A61B 6/5217* (2013.01)

(58) Field of Classification Search
CPC ........ A61B 6/00; A61B 6/032; A61B 6/035; A61B 6/482; A61B 6/4241; G01N 23/04; G01N 23/046; G01T 1/24; G01T 1/247; G01T 1/2928; G01T 1/2985; G06T 11/005
USPC ........................ 378/5, 19, 901; 250/370.09
See application file for complete search history.

(56) References Cited

U.S. PATENT DOCUMENTS

| | | |
|---|---|---|
| 4,029,963 A | 6/1977 | Alvarez et al. |
| 8,183,535 B2 | 5/2012 | Danielsson et al. |
| 8,378,310 B2 | 2/2013 | Bornefalk et al. |
| 2008/0315106 A1 | 12/2008 | Buchinsky |

OTHER PUBLICATIONS

Stevens et al., "Depth-segmented detector for x-ray absorptiometry" Med Phys 27(5), May 2000, pp. 1174-1184.
Roessl et al., "Edge-on semiconductor x-ray detectors—towards high-rate counting computed tomography", 2008 IEEE Nuclear Science Symposium, 2008, pp. 1741-1751.
Bornefalk et al, "Photon-counting spectral computed tomography using silicon strip detectors: a feasibility study", Phys Med Biol vol. 55, 2010, pp. 1999-2022.
Alvarez, Robert E., "Estimator for photon counting energy selective x-ray imaging with multibin pulse height analysis," Medical Physics, 38(5), 2011, pp. 2324-2334.
Herrmann et al., "Performance simulation of an x-ray detector for spectral CT with combined Si and Cd[Zn]Te detection layers," Phys Med Biol. 55(24), 2010, pp. 7697-7713.
Persson et al., "Energy-resolved CT imaging with a photon-counting silicon-strip detector," Phys. Med. Biol. 59, Oct. 2014, pp. 6709-6727.
Yao et al., "Use of Depth Information from In-depth Photon Counting Detectors for X-ray Spectral Imaging: A Preliminary Simulation Study," Medical Imaging 2014: Physics of Medical Imaging, Proc. of SPIE vol. 9033, Mar. 2014.
Yao et al., "Utilization of In-Depth Photon Counting Detectors Towards X-Ray Spectral Imaging: The Benefits From the Depth Information," 2014 IEEE 11th International Symposium on Biomedical Imaging (ISBI), Apr. 29-May 2, 2014 pp. 1156-1159.

*Primary Examiner* — Jurie Yun
(74) *Attorney, Agent, or Firm* — Lumen Patent Firm

(57) ABSTRACT

Spectral x-ray imaging using a photon counting x-ray detector (PCXD) transmits a broad spectrum x-ray beam through an object, detects the transmitted x-ray beam with the PCXD and processes the detected signals to determine material characteristics of the object using both the detected signals as a function of detector layer and the detected signals as a function of the particular energy band. Each detector layer of the multiple detector layers produces at least two signals, each signal representing a detected x-ray intensity in a particular energy band, and the depth information contained in the separate read-out channels.

10 Claims, 5 Drawing Sheets

SPECTRAL IMAGING SYSTEM AND METHOD

CROSS-REFERENCE TO RELATED APPLICATIONS

This application claims priority from U.S. Provisional Patent Application 61/917,929 filed Dec. 18, 2013, which is incorporated herein by reference.

FIELD OF THE INVENTION

This invention relates generally to spectral x-ray detection and imaging. More specifically, it relates to improved systems and methods for determining material characteristics from x-ray measurements using photon counting detectors.

BACKGROUND OF THE INVENTION

Traditional x-ray imaging techniques employ integrating detectors that detect the total intensity of a transmitted beam through an object to be imaged. Because different materials (such as bone and tissue) attenuate the x-ray beam by different amounts, the resulting detected intensity will vary accordingly. In order to improve the ability to discriminate between materials, spectral x-ray imaging techniques have been developed. These techniques allow for enhanced discrimination between different materials by taking advantage of the energy dependence of the attenuation of x-rays. Because the attenuation of x-rays by a material has an energy (spectrum) dependence that is different among materials, spectral information can be used to enhance discrimination between materials. For example, two materials that have the same attenuation at one x-ray energy may have distinct attenuations at another x-ray energy, thereby allowing them to be discriminated.

One older approach to spectral imaging involves imaging an object using an x-ray beam switched between two distinct energies and detecting images using traditional integrating detectors. Combining the images at these two energies allows for improved discrimination between characteristics of materials in the object being imaged. One disadvantage of this approach is that the two images are not simultaneous.

Another approach to spectral imaging uses a single broad spectrum kVp x-ray beam and energy-discriminating detectors. These are described in U.S. Pat. No. 4,029,963 to Alvarez and Macovski, incorporated herein by reference. The patent describes one approach wherein the detector is divided into layers in the direction of x-ray travel. Since lower energy x-rays tend to be absorbed more easily than higher energy x-rays, the front layer will detect x-rays with a lower effective energy than the back layer. This has been generalized to more than two layers, e.g. see Stevens and Pelc, Medical Physics, vol 27, pp 1174-84, 2000. While these layered detectors provide spectral information, the energy separation is not ideal and there is significant overlap in the spectra detected in the various layers.

Photon counting x-ray detectors (PCXD) with energy discriminating capabilities are the most promising type of detector for this approach to spectral x-ray imaging, primarily because they provide high dose-efficiency due to elimination of electronic noise, and the potential for energy discrimination, the latter being especially important for spectral imaging.

Photon counting x-ray detectors, however, have a relatively slow counting rate that causes count losses and pulse pile-up. To reduce photon saturation effects caused by the insufficient counting speed, a multi-layer ("in-depth") detector system with separate read-out channels has been proposed to improve the speed. Specifically, Roessl et al. proposed an edge-on cadmium-zinc-telluride (CZT) detector with multiple layers of different thicknesses and individual read-out channels for each layer. Improving upon this approach, Bornefalk et al. validated the feasibility of edge-on silicon (Si) strip detectors, which are more economical and easier to fabricate, to achieve even higher pile-up-free count rate. In effect, these layered detectors are designed to solve the saturation problem of photon-counting type detectors by distributing the detection load among separate material layers. The separate signals from the different read-out channels are combined, and the resulting net signal, which is similar to that from a single fast-counting thick layer, is used for material characterization.

Despite progress in overcoming the limited counting rate of PCXDs, there remain other limiting factors of energy discriminating PCXDs. For example, one such limitation is the imperfect energy response of the detector material. Detected photons may produce signals lower than their actual energy due to Compton scatter events, K-escape, charge-sharing, and other phenomena. For example, in silicon (Si) a large fraction of the detected signals might be Compton scatter events while K-escape can be important in cadmium-telluride (CdTe) and cadmium-zinc-telluride (CZT) detectors. Some of these degradations are seen in detectors operating in other modes (e.g., energy integrating), but become more critical in PCXDs due to the expected energy discrimination.

In view of the above, there remains a need for further improvements in spectral x-ray imaging detectors and imaging techniques.

SUMMARY OF THE INVENTION

Known multi-layer PCXD techniques use depth segmentation merely to overcome the counting rate limit of the detector by reducing the counting burden on each layer. In those techniques, the measurement from all the layers are combined into a single spectrum prior to spectral analysis, as that suffices for the purposes of addressing the counting rate problem. In addition, assuming an ideal energy response of the PCXD, retaining depth-specific data from the PCXDs provides no additional information, and such depth information would not be expected to have any benefit. Consequently, none of the known multi-layer PCXD techniques retain the depth information from the separate layers or propose to use it to improve spectral imaging.

In all of these, depth segmentation was used to increase the counting rate of the detector, but the spectral information came only from photon counting. The spectral information from all the layers is combined and the depth dependence of the spectra is not retained. Since photon counting is believed to be superior to depth segmentation for energy analysis, there would seem to be no benefit to using the depth response for energy information. However, the energy response of currently achievable photon counting detectors is imperfect. The current invention comes from the realization that the depth segmentation that may have been designed into the detector to achieve high count rate can also improve the overall energy response.

In contrast with conventional understanding, the present inventor realized that, surprisingly, the performance of a depth-segmented photon counting detector could in fact be improved if the depth dependence of the spectral data was retained and appropriately utilized. For PCXDs with imperfect energy response the improvement can be significant.

For example, with a silicon strip PCXD, some detected photons deposit all or the vast majority of their energy in the detector. These "photopeak" events contribute to a very useful characterization of the spectrum. However, many photons scatter in the detector and deposit only a fraction of their energy. With the prior art methods these events are not very useful for energy analysis. However, the depth distribution of these events, if retained and appropriately analyzed, can be used to supplement that from the photopeak events.

Accordingly, in one aspect, the present invention provides depth segmentation and photon counting devices and methods to obtain material-specific or spectral information from x-ray measurements by utilizing energy information from both photon counting and depth response. The simultaneous use of energy information from photon counting and from depth response provide surprising advantageous improvements for spectral x-ray imaging and material characterization.

In one aspect, the present invention provides a device for spectral x-ray measurement that includes an x-ray source, a multi-layer photon counting x-ray detector (PCXD), and electronics (e.g., a computer and/or signal processing circuits) connected to the detector. The x-ray source is configured to transmit a broad spectrum x-ray beam through an object, and the photon counting x-ray detector (PCXD) is configured to detect the transmitted x-ray beam to produce detected signals. The photon counting x-ray detector (PCXD) has multiple detector layers such that each detector layer of the multiple detector layers produces at least two signals, each signal representing a detected x-ray intensity in a particular energy band. The computer is configured to process the detected signals to produce a value representative of material characteristics of the object by using both the detected signals as a function of detector layer and the detected signals as a function of the particular energy band. More specifically, the computer may decompose the detected signal into a linear combination of two selected basis materials using depth information contained in separate read-out channels of the multiple detector layers. Preferably, the PCXD is a multiple-layer depth-segmented energy-discriminating photon counting x-ray detector system. In some embodiments, the x-ray source and PCXD are components of a CT system.

In another aspect, the invention provides a method for spectral x-ray measurement using a photon counting x-ray detector (PCXD). The method includes transmitting from an x-ray source a broad spectrum x-ray beam through an object, detecting the transmitted x-ray beam with the photon counting x-ray detector (PCXD) to produce detected signals, and processing with a computer the detected signals to produce a value representative of material characteristics of the object using both the detected signals as a function of detector layer and the detected signals as a function of the particular energy band. The detecting uses multiple detector layers in the PCXD to produce the detected signals such that each detector layer of the multiple detector layers produces at least two signals, each signal representing a detected x-ray intensity in a particular energy band. The detecting the transmitted x-ray beam preferably detects the attenuated x-ray signals with a multiple-layer depth-segmented energy-discriminating photon counting x-ray detector system. In some embodiments, the transmitting from an x-ray source the broad spectrum x-ray beam is realized by performing a scan of an object using a CT system. The processing with a computer to process the detected signals to produce the value representative of material characteristics of the object preferably includes decomposing the detected signal into a linear combination of at least two selected basis materials, and the decomposing uses the depth information contained in the separate read-out channels.

In yet another aspect, the invention provides a method for spectral x-ray imaging using a photon counting x-ray detector (PCXD). The method includes performing an x-ray scan of an object and decomposing the detected signal into a linear combination of at least two selected basis materials. Performing the scan comprises i) detecting by a multiple-layer depth-segmented energy-discriminating photon counting x-ray detector system a signal representing an attenuation of the object in at least two energy bands, where the multiple layers have separate read-out channels, and where the signal comprises detected events grouped into energy bins and preserves depth information contained in the separate read-out channels. The decomposing then uses the depth information contained in the separate read-out channels for determining material characteristics of the object. The x-ray scan of an object may include, for example, performing a computed tomography (CT) scan with a CT system.

DETAILED DESCRIPTION

The significance of the present invention can be appreciated by first considering the design of known devices and techniques for spectral x-ray imaging.

Figure 1:
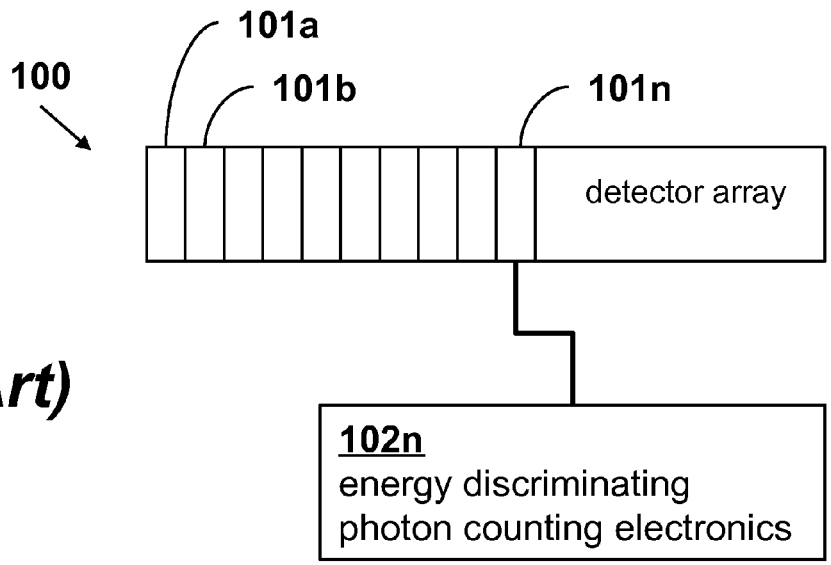
FIG. 1 is a schematic block diagram of a conventional multi-element photon counting detector array and energy discriminating photon counting electronics.

FIG. 1 shows a conventional photon counting detector array 100. While spectral imaging can be accomplished using only a single detector element, generally, especially for CT systems, a plurality of spatially distributed detector elements 101a, 101b, . . . 101n, etc. are included in detector array 100. Each element of the photon counting energy discriminating detector 100 is connected to energy discriminating photon counting electronics. Shown in FIG. 1 is detector element 101n connected to electronics 102n that process the detector signals from that element. Although not shown, each element is similarly connected to its own signal processing electronics.

Figure 2:
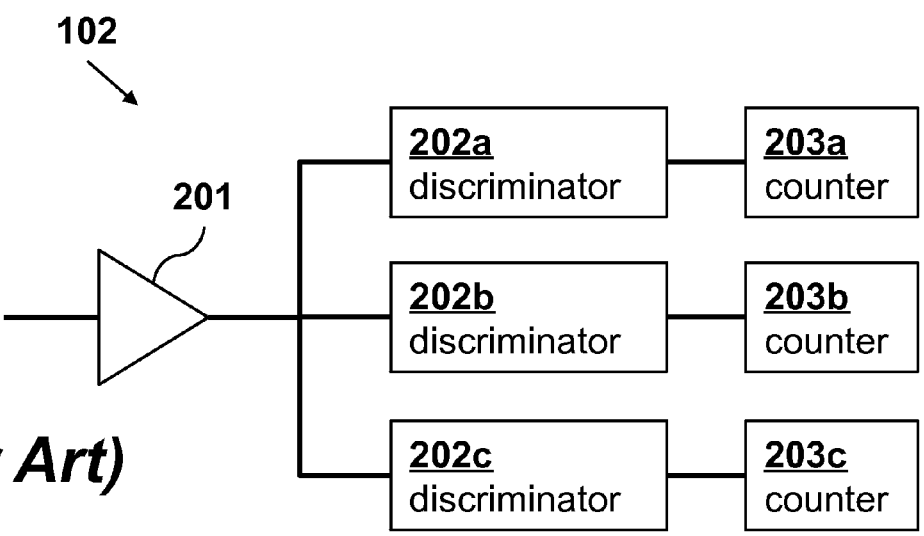
FIG. 2 is a schematic block diagram detailing the energy discriminating photon counting electronics for one detector element of FIG. 1.

The electronics of a representative processing channel, such as 102n of FIG. 1, are shown in more detail in FIG. 2 and named 102 in that figure. The signal from each element of the detector is first processed by a pulse shaping amplifier 201 whose design is known in the art. The shaped pulse is sent to multiple discriminators. In the figure, three discriminators 202a, 202b, 202c are shown but more or fewer discriminators can be used. The discriminators compare the amplitude of the pulse to multiple respective reference voltages. The simplest discriminator design simply compares the amplitude of the input pulse to a single reference voltage and outputs a pulse when the input pulse exceeds the reference voltage. Counters 203a, 203b, 203c are provided to count the number of events identified by each corresponding discriminator. For richer spectral measurements, the output of the shaping amplifier 201 is processed by additional discriminators, each with a different reference voltage. Each discriminator-counter pair thus represents a distinct energy channel. The result of all the counters 203a, 203b, 203c allows information about the detected spectrum to be extracted using techniques known in the art. For example, the measured counts as function of energy channel (discriminator) are combined to estimate the amounts of two or more basis materials. One technique that is known to be accurate and precise uses a Maximum Likelihood Estimator (MLE). An alternative technique that can be computationally more efficient is to use polynomial combinations of the logarithms of the counts at different energies. Some possible techniques are discussed in "Estimator for photon counting energy selective x-ray imaging with multibin pulse height analysis" by Robert E. Alvarez, Medical Physics, 38(5): 2324-2334, 2011, and in the references cited in that paper.

Often, "energy bins" are considered as events in which the amplitude is above a lower level threshold and also below a higher level limit. These can be calculated from single threshold counts as the difference between two counters. If two counters with single low energy thresholds of E1 and E2 are subtracted, the result is the number of counts with amplitude between E1 and E2.

The energy information is used in this way to obtain material characterization information. This can be, for example, the effective atomic number and the electron density, the amount of two or more "basis materials," or an estimate of what would have been measured if a specific material were cancelled. All of these types of material characterization estimates based on spectral x-ray measurements are known in the art.

Figure 3:
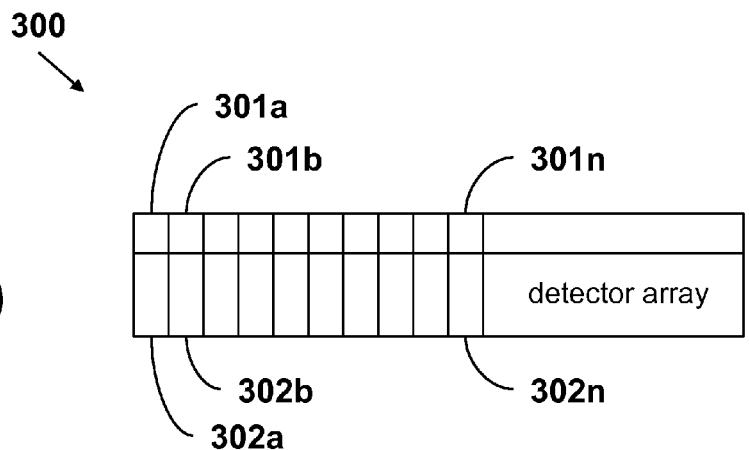
FIG. 3 is a schematic block diagram of a conventional multi-layer energy integrating spectral detector array.

FIG. 3 shows a different design for a conventional spectral detector 300. In this design, each detector element is an integrating type detector divided into two (or more) layers. Again, while spectral measurements can be made by a single multi-layer detector element, often an array of such elements is used. In the array of FIG. 3 the elements have two layers, but more layers could be used. A first element has front layer 301a and back layer 302a, a second element has front layer 301b and back layer 302b, and the n-th element of the array has front layer 301n and back layer 302n. Each layer of each element is connected to a conventional energy integrating detector electronic channel (not shown). The data from the multiple layers are processed to produce material characteristic values. These computation methods are analogous to those described above for photon counting energy discriminating detectors.

The spectral detectors of the type shown in FIG. 1 (single-layer energy discriminating photon counting detector) and of the type shown in FIG. 3 (multi-layer energy integrating detector) are conventionally viewed as alternative strategies for obtaining spectral information.

A known limitation of photon counting detectors of FIG. 1 is their limited counting rate. These detectors do not perform well if the rate of incident photons approaches and exceeds a value set by the design of the detector and the processing electronics. One technique to increase the count rate capability of a photon counting detector is to segment the detector into multiple layers, with each layer counting independently. This is described in "Performance simulation of an x-ray detector for spectral CT with combined Si and Cd[Zn]Te detection layers" by Herrmann C, Engel K J, and Wiegert J., Phys Med Biol. 55(24):7697-713, 2010 and also in "Energy-resolved CT imaging with a photon-counting silicon-strip detector" by Mats Persson, Ben Huber, Staffan Karlsson, Xuejin Liu, Han Chen, Cheng Xu, Moa Yveborg, Hans Bornefalk and Mats Danielsson, Phys. Med. Biol. 59: 6709-6727, 2014. In the detector in the Persson paper, each element is divided into 16 depth segments (layers) and each layer of each element is processed by electronics that counts events using eight discriminators. However, the separation into layers is used only to increase the counting rate capability and not to provide additional energy information. Because the system already has energy discrimination in each of the photon counting channels, conventional wisdom would not expect benefit from using layer information for energy discrimination. Therefore, in conventional designs, the count information in the various layers of each element are combined before processing for material characterization. This processing technique is illustrated by the circuit in FIG. 4, which shows a single detector element segmented into three layers 401a, 401b, 401c. The signals from the layers are processed by corresponding energy discriminating photon counting electronics 402a, 402b, 402c. Significantly, the counts from these discriminators are combined in 403. It is important to note that 403 maintains the energy discrimination information but does not maintain any layer-dependent information. The combined energy information from all the layers is then processed in block 404 to compute material characterization information as described previously.

Figure 4:
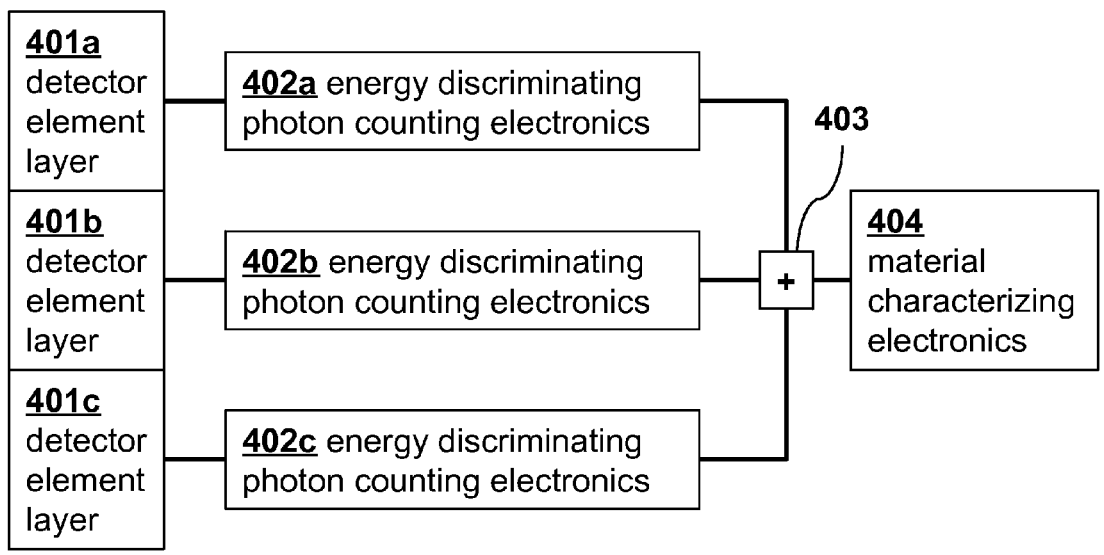
FIG. 4 is a schematic block diagram of a conventional multi-layer photon counting detector and energy discriminating photon counting channels whose signals are combined prior to processing for material characterization.
Figure 5:
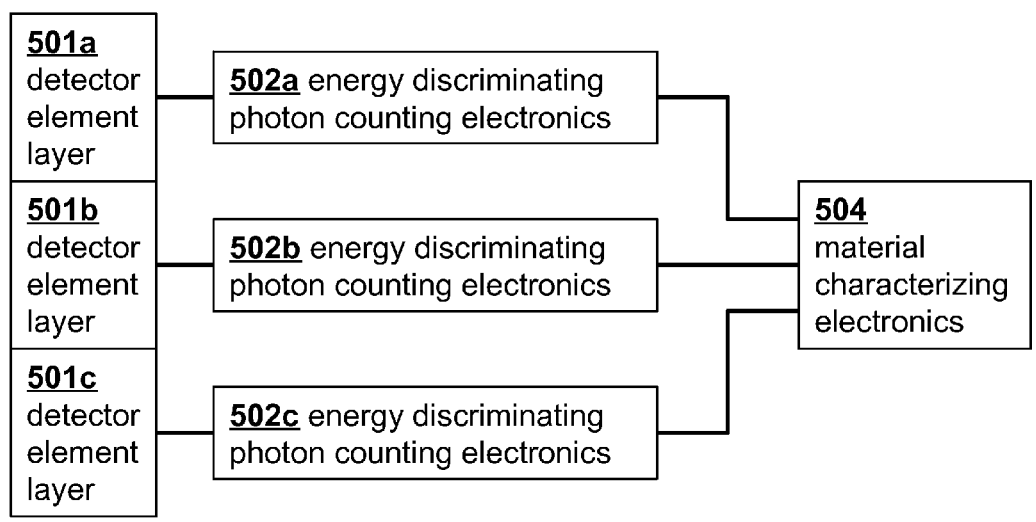
FIG. 5 is a schematic block diagram of a multi-layer photon counting detector and energy discriminating photon counting channels whose depth-dependence is retained and used to improve processing for material characterization.

The present invention rests on the surprising realization that the layer-dependence of the counts can in many instances provide additional material characterization information. Specifically, in contrast to the prior art systems, the counts in the various layers are kept separate. This design is shown in FIG. 5, which, as with FIG. 4, shows a single detector element segmented into three layers 501a, 501b, 501c. The signals from the layers are processed by corresponding energy discriminating photon counting electronics 502a, 502b, 502c. The counts from each of these discriminating counter channels, however, are not all added. Rather, the counts are separately provided without summing (i.e., maintaining layer-dependent information) to the computation system 504 to compute material characterization information.

One computation method that can be used to produce the material characterization information is again a Maximum Likelihood Estimator (MLE). Alternative methods are to use polynomials of the logarithms of the counts in each energy channel of each layer. The method proposed by Alvarez in the reference cited above can be adapted to this task as well.

Figure 6:
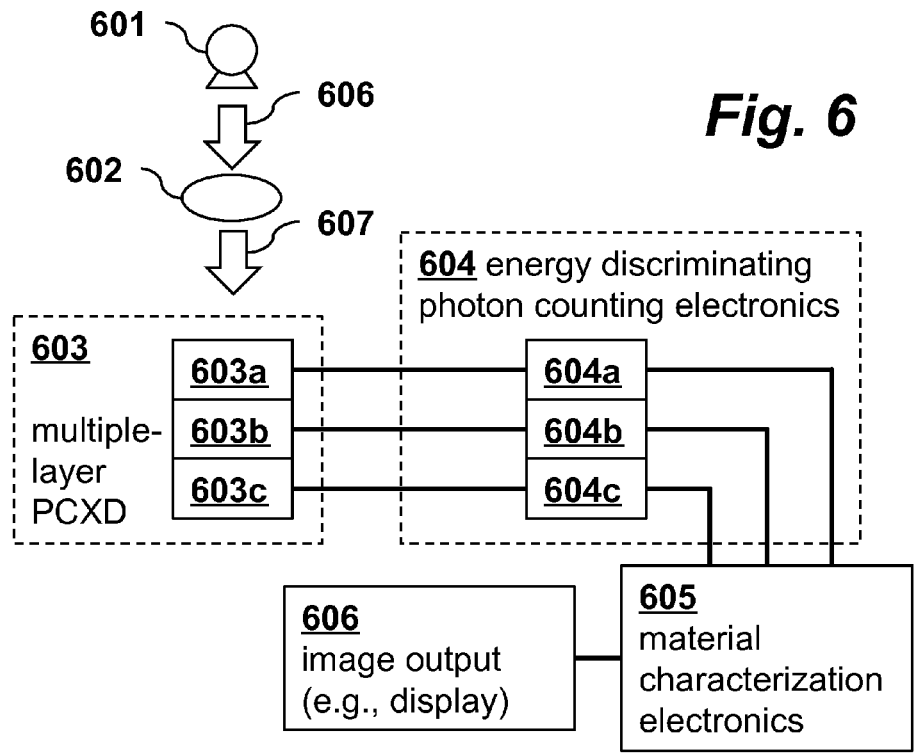
FIG. 6 is an apparatus for spectral x-ray measurement and material characterization using a multi-layer photon counting x-ray detector, according to an embodiment of the invention.

An apparatus implementing the techniques of the present invention is shown in FIG. 6. The system has an x-ray source 601 that produces a broad spectrum x-ray beam 606. An object to be measured 602 is illuminated with the x-ray beam 606 and the transmitted x-rays 607 are measured by a multiple-layer photon counting energy discriminating x-ray detector 603. The detector 603 may have a single element (as shown) or it can have multiple elements. In one embodiment, the PCXD detector is made of CdTe. In another it is made of Si. In one embodiment, the in-depth detector element may be composed of ten layers with the same total thickness of the corresponding single layer detector. The depth segmentations (thicknesses of the layers) may be calculated to have each layer detect approximately 10% of the photons in beam 607 transmitted by the object and incident on the detector.

In any case, each detector element is divided into multiple layers, such as 603a, 603b, 603c in FIG. 6. The output of detector 603 is provided to photon counting energy discriminating electronics 604. Each layer of each detector element 603a, 603b, 603c has its own separate corresponding photon counting energy discriminating electronics 604a, 604b, 604c. The output from each of the photon counting energy discriminating electronics channels 604a, 604b, 604c is separately provided (i.e., preserving detector-layer information) to electronics 605 that computes the material characterization information of object 602 using both the energy count information and the depth (layer) information. This module 605 can be a computer programmed to execute an appropriate algorithm. The MLE is one such algorithm but other algorithms can be used. If the system is an imaging system (e.g., CT imaging system), images formed from material characterization information are produced and displayed on an output device 606. The system can be a computed tomography system, or it can be a projection measurement system, such as an absorptiometry system (DEXA) used to measure bone mineral density.

Figure 7:
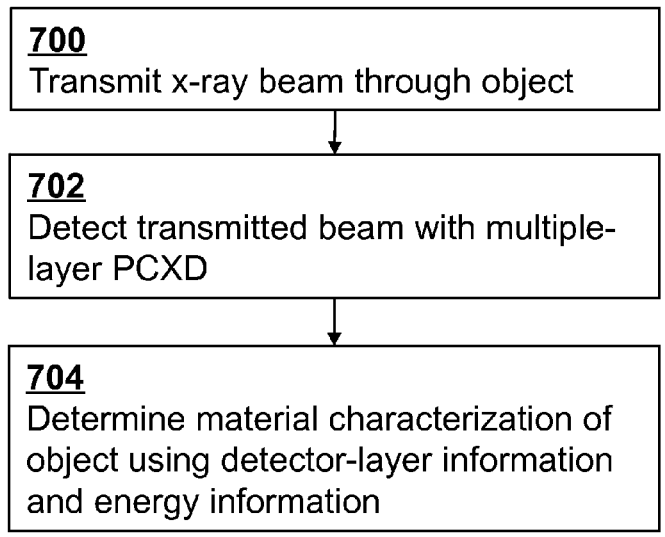
FIG. 7 is an outline of the steps of a method for spectral x-ray measurement and material characterization using a multi-layer photon counting x-ray detector, according to an embodiment of the invention.

FIG. 7 is an outline of the steps of a method for spectral x-ray measurement using a photon counting x-ray detector, according to an embodiment of the invention. In step 700 a broad spectrum x-ray beam is transmitted from an x-ray source through an object. In step 702 the transmitted x-ray beam is detected with the photon counting x-ray detector (PCXD) to produce detected signals. The detecting uses multiple detector layers in the PCXD to produce the detected signals such that each detector layer of the multiple detector layers produces at least two signals, each signal representing a detected x-ray intensity in a particular energy band. In step 704 the detected signals are processed by electronics (such as an appropriately programmed computer) to produce a value representative of material characteristics of the object. The processing uses both the detected signals as a function of detector layer and the detected signals as a function of the particular energy band.

Material separation and characterization by spectral x-ray measurements requires that the x-ray spectrum transmitted through the object contain a range of energies to enable separation of the various materials in the object based on their distinctive spectral responses. Material separation or characterization requires that different materials have different energy dependence to their attenuation. In general, the spectrum of the x-ray source needs to be broad enough to contain energies that are different enough for the material differences to be detected. With a beam containing only x-ray photons of the same energy (monoenergetic x-rays), for example, any material behaves like a multiple of another material. That is, material A cannot be discriminated from material B of a suitable density. To reliably separate A from B, x-ray photons with different energies are needed so that the transmission of x-rays as a function of energy can be used to distinguish A from B. The discrimination ability generally improves with increasing separation of the x-ray energies (so long as they are still transmitted through the object in sufficient quantity). One guideline is for the spectrum to be broad enough to contain some photons that interact primarily by one energy dependent physical process (e.g., photoelectric absorption) and others that interact primarily by another physical process with another energy dependence (e.g., Compton scattering). Materials with different ratios of photoelectric absorption to Compton scattering can then be resolved. The spectra from conventional x-ray tubes have a broad spectrum. In practice, an x-ray spectrum with a width of greater than 10 keV is defined as being broad, and sufficient for the purposes of spectral imaging.

Within the diagnostic energy range, x-rays interact with materials mainly through two physical mechanisms, the photoelectric effect and Compton scattering. Spectral x-ray imaging is based on these two interactions and, in the absence of K-edges, the attenuation of any material can be decomposed into a linear combination of these two mechanisms, or as a linear combination of any other two materials without K-edges:

$$\mu(E)t = \mu_1(E)t_1 + \mu_2(E)t_2 \quad (1)$$

where $\mu_1$ and $\mu_2$ are the attenuation coefficients of the two selected "basis" materials and $t_1$ and $t_2$ are the respective thicknesses, which characterize the unknown material. To estimate the amount of the two basis materials, the attenuation of the object in at least two energy bands is measured. Each follows the Beer-Lambert law $$\phi(E) = \phi_0(E)\exp\{-\mu_1(E)t_1 - \mu_2(E)t_2\} \quad (2)$$

The signal detected by an M-layer in-depth PCXD system, discretized to 1 keV steps, is given by:

$$\phi_i = R_K Q_{K,i} D_{K,i-1} O_K \phi_{0,K} \quad (3)$$

where $\phi_{0,K} = [\phi_0(1), \ldots, \phi_O(K)]^T$ denotes the output spectrum from the x-ray source (e.g., 120 kVp), $O_K = \text{diag}(\exp(-\mu \cdot t))$ is the attenuation of the object in which $\mu = [\mu_1, \mu_2]$ is the attenuation coefficients of the two basis materials and $t = [t_1, t_2]^T$ represents the thickness of each, $D_{K,i-1} = \text{diag}(\exp(-\mu_d \Sigma_l d_l))$ is the detectors' self-attenuation (where the sum is from l=0 to i-1), and $Q_{K,i} = I - \text{diag}(\exp(-\mu_d d_i))$ accounts for the detection efficiency of the i-th layer with $\mu_d$ being the attenuation coefficient of the detector and $d_i$ being the thickness of the i-th layer ($d_0 = 0$), $R_K$ is energy response matrix composed of energy response functions (ERFs) evaluated at each input and apparent energy pair, $(U_K, E_K)$, as further described below, $U_K = E_K = (1, 2, K)^T$ is the energy vector at 1 keV increments, and $\phi_i = [\phi_i(1), \ldots, \phi_i(K)]^T$ is the detected spectrum from the i-th layer of the PCXDs.

Generally, detected events are grouped into energy bins by separate energy discriminating counter channels. The counts in the j-th energy bin for the i-th layer are:

$$\psi_{i,j} = \Sigma_k \phi_i(k), \quad (4)$$

where $0 \leq b_1 < b_2 < \ldots < b_N \leq K$ are the energy bin (discriminator) thresholds, and the sum is from $k = b_{j-1}$ to $b_{j+1}$.

From the detected signals, the amount of the two materials can be estimated using maximum-likelihood method (MLE) using a Poisson noise model $$t^* = \text{argmax}_{\mu_1, \mu_2, \mu_d, t_d, R}\{l < t | \nu >\} \quad (5)$$

and the log-likelihood function after omitting the constant term is more explicitly written as $$l<t|v> = \log(L<v|t>) = \Sigma_{i=1,M} \Sigma_{j=1,N} (-\psi_{i,j} + v_{i,j} \log \psi_{i,j}) \quad (6)$$

where $v_{i,j}$ as measured from the j-th bin and the i-th layer is a Poisson random variable, parameterized by $\psi_{i,j}$.

Figure 8:
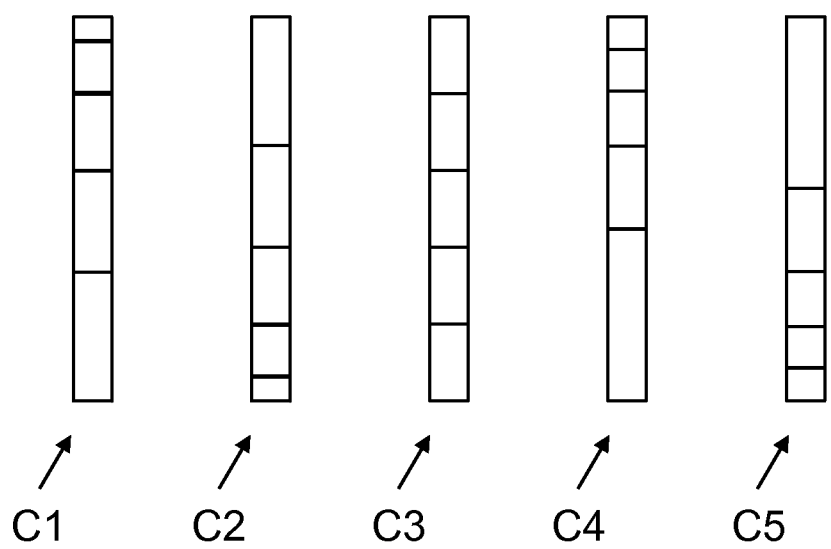
FIG. 8 is a schematic diagram illustrating five segmentation configurations for a multi-layer energy discriminating photon counting detector, according to embodiments of the present invention.

Simulation studies were performed to examine the benefits of the novel technique disclosed herein. To further illustrate using a concrete example, consider transmitting a 120 kVp spectrum through an object comprised of tissue and bone to generate the spectrum incident on a PCXD, with the material decomposition basis materials being water and calcium. PCXDs ranging from a single thick layer up to 9 layers were studied (e.g., 3.2 cm for Si, 0.5 cm for GaAs and 0.3 cm for CdTe). For comparison, consider five embodiments corresponding with five segmenting configurations, as shown in FIG. 8, where the thicknesses of each layer (depicted in the figure by rectangles) are calculated according to the segmentation and the total number of layers. The five configurations include a linearly increasing and decreasing depth segmentation (C1, C2), equal thickness segmentation (C3), an equal quanta segmentation (C4) with layers getting thicker with depth such that each layer attenuates equal proportion of photons transmitted by the object and incident on the detector, and a reverse segmentation (C5) with the same thickness elements as the equal quanta but are flipped. These segmentations are shown in FIG. 8 for an example with five layers. The segmentation labeled C1 has layer thicknesses that increase linearly from top (the x-ray entry surface) to bottom while that labeled C2 is reversed. C3 has layers of equal thickness. The layer thicknesses for the segmentation labeled C4 are designed so that each layer detects a roughly similar number of photons. Segmentation C5 has the same thicknesses as C4 but reversed.

For ideal PCXDs with ideal energy response and full spectral resolution, the depth information is not expected to be beneficial to the material decomposition. The reason for this is that a PCXD with an ideal energy response function (ERF) extracts all the information present in the transmitted spectrum and the depth dependence cannot contribute additional information. When an imperfect ERF is considered, however, the in-depth detector outperforms the single layer detector (or the in-depth detector in which the depth dependence is discarded) for all detector materials. The benefits from the depth information vary and the improvements are spectrum dependent. The more corrupted the information, the larger the benefits.

The five depth segmenting configurations (C1-C5) result in essentially the same CLRBs as the single layer when ideal ERF is assumed; this is expected since the depth data adds no information. Their performances differentiate when spectral distortion is present. Nine depth layers with equal quanta segmentation (C4) is optimal across all threshold energies for 2 bins but is nonetheless worse than the ideal case (perfect ERF). On the other hand, the worst case (3 layers and C3) is better than no segmentation. For each configuration, increasing the number of depth segments improves the performance.

The optimal binning threshold depends on the way the in-depth PCXDs are segmented and also on detector materials. The commonly picked thresholding energy separating the low and high energy counters (~60 keV) is actually a terrible choice for a 2 energy bin Si detector. In fact, the severe Compton scattering of high energy photons in Si causes the average true photon energy of the two bins with a 60 keV threshold to be similar. The optimum is achieved when the average energies are more separated plus the x-ray quanta are more balanced between the low and high bins. This is difficult to achieve with Si and only two energy bins. A threshold with equal counts in the low and high energy bins is likely to simply separate the Compton and photopeak portions of the spectrum and achieve similar effective photon energies in the two bins, as discussed above. A threshold that splits the photopeak spectrum will have different effective energies in the two bins but will have unequal number of counts. This compromise is avoided if more than two energy channels are used.

In summary, assuming imperfect energy response (ERF), the in-depth detector outperforms the single layer detector (or the in-depth detector in which the depth dependence is discarded). The improvement is spectrum dependent. The broader the transmitted spectrum (e.g. less filtration or thinner object) the larger the benefit. The depth information contributes most when the ERF degrades the performance of PCXDs most severely.

Depth information is beneficial to the material decomposition for PCXDs with imperfect ERF. The benefit is negatively correlated with the spectral distortion for PCXD.

Embodiments of the invention have applications to computed tomography and projection x-ray imaging for medical and other applications, such as security screening. The techniques of the invention would be of direct benefit to silicon strip detectors for spectral CT and other detector technologies.

The invention claimed is:

1. A method for spectral x-ray measurement using a photon counting x-ray detector (PCXD), the method comprising:
    transmitting from an x-ray source a broad spectrum x-ray beam through an object;
    detecting the transmitted x-ray beam with the photon counting x-ray detector (PCXD) to produce detected signals, wherein the detecting uses multiple detector layers in the PCXD to produce the detected signals such that each detector layer of the multiple detector layers produces at least two signals, each signal representing a detected x-ray intensity in a particular energy band;
    processing with a computer the detected signals to produce a value representative of material characteristics of the object, wherein the processing uses both the detected signals as a function of detector layer and the detected signals as a function of the particular energy band.

2. The method of claim 1
    wherein transmitting from an x-ray source the broad spectrum x-ray beam comprises performing a kV x-ray scan of an object using a CT system.

3. The method of claim 1
    wherein detecting the transmitted x-ray beam with the photon counting x-ray detector (PCXD) comprises detecting attenuated x-ray signals with a multiple-layer depth-segmented energy-discriminating photon counting x-ray detector system.

4. The method of claim 1
    wherein processing with a computer the detected signals to produce the value representative of material characteristics of the object comprises decomposing the detected signal into a linear combination of two selected basis materials; wherein the decomposing uses depth information contained in separate read-out channels of the multiple detector layers.

5. A device for spectral x-ray measurement comprising:
an x-ray source configured to transmit a broad spectrum x-ray beam through an object;
a photon counting x-ray detector (PCXD) configured to detect the transmitted x-ray beam to produce detected signals; wherein the photon counting x-ray detector (PCXD) has multiple detector layers such that each detector layer of the multiple detector layers produces at least two signals, each signal representing a detected x-ray intensity in a particular energy band;
a computer configured to process the detected signals to produce a value representative of material characteristics of the object, wherein the computer is further configured for processing the detected signals to use both the detected signals as a function of detector layer and the detected signals as a function of the particular energy band.

6. The device of claim 5 wherein the x-ray source and PCXD are components of a CT system.

7. The device of claim 5 wherein the PCXD is a multiple-layer depth-segmented energy-discriminating photon counting x-ray detector system.

8. The device of claim 5 wherein the computer is configured to decompose the detected signal into a linear combination of two selected basis materials using depth information contained in separate read-out channels of the multiple detector layers.

9. A method for spectral x-ray imaging using a photon counting x-ray detector (PCXD), the method comprising:
performing an x-ray scan of an object; wherein performing the scan comprises i) detecting by a multiple-layer depth-segmented energy-discriminating photon counting x-ray detector system a signal representing an attenuation of the object in at least two energy bands; where the multiple layers have separate read-out channels; where the signal comprises detected events grouped into energy bins and preserves depth information contained in the separate read-out channels;
decomposing the detected signal into a linear combination of two selected basis materials; wherein the decomposing uses the depth information contained in the separate read-out channels.

10. The method of claim 9 wherein performing an x-ray scan of an object comprises performing a computed tomography (CT) kV x-ray scan with a CT system.

* * * * *